(12) United States Patent
Haverinen et al.

(10) Patent No.: US 12,100,965 B2
(45) Date of Patent: Sep. 24, 2024

(54) UNIVERSAL CHARGER

(71) Applicant: Oura Health Oy, Oulu (FI)

(72) Inventors: Teemu Juhani Haverinen, Oulu (FI); Heikki Juhani Huttunen, Haukipudas (FI); Kari Kuisma Kanniainen, Ii (FI); Sauli Hannes Flander, Helsinki (FI); Ari Aukusti Jarvinen, Kempele (FI); Antti Pekka Saikkonen, Haukipudas (FI)

(73) Assignee: Oura Health Oy, Oulu (FI)

( * ) Notice: Subject to any disclaimer, the term of this patent is extended or adjusted under 35 U.S.C. 154(b) by 412 days.

(21) Appl. No.: 17/493,774

(22) Filed: Oct. 4, 2021

(65) Prior Publication Data

US 2023/0105636 A1    Apr. 6, 2023

(51) Int. Cl.
*H02J 7/00* (2006.01)
*H02J 50/00* (2016.01)
*H02J 50/10* (2016.01)
*H02J 50/90* (2016.01)

(52) U.S. Cl.
CPC .......... *H02J 50/005* (2020.01); *H02J 7/0044* (2013.01); *H02J 50/10* (2016.02); *H02J 50/90* (2016.02)

(58) Field of Classification Search
CPC .......... H02J 50/005; H02J 50/10; H02J 50/90; H02J 7/0044
USPC .......................................... 320/108; 307/104
See application file for complete search history.

(56) References Cited

U.S. PATENT DOCUMENTS

2017/0070076 A1*    3/2017    Karanikos ............. H02J 7/0042

* cited by examiner

*Primary Examiner* — Zixuan Zhou
(74) *Attorney, Agent, or Firm* — Holland & Hart LLP

(57) ABSTRACT

Methods, systems, and devices for wireless charger are described. A charging device may include a base configured to receive a ring-shaped wearable device in multiple radial orientations relative to the base. The charging device may also include a magnetic component configured to magnetically attract a magnetic component of the ring-shaped wearable device to orient the wearable device in a single radial orientation relative to the base. The charging device may include an inductive charging component that may wireless charge the wearable device via an inductive charging component of the wearable device based on the inductive charging components being within a threshold distance.

27 Claims, 9 Drawing Sheets

UNIVERSAL CHARGER

FIELD OF TECHNOLOGY

The following relates to wearable devices and data processing, including a universal charger.

BACKGROUND

Some wearable devices may be configured to collect physiological data from users, including temperature data, heart rate data, and the like. However, poor connection with a charging device may prevent the wearable device from charging.

DETAILED DESCRIPTION

Figure 1:
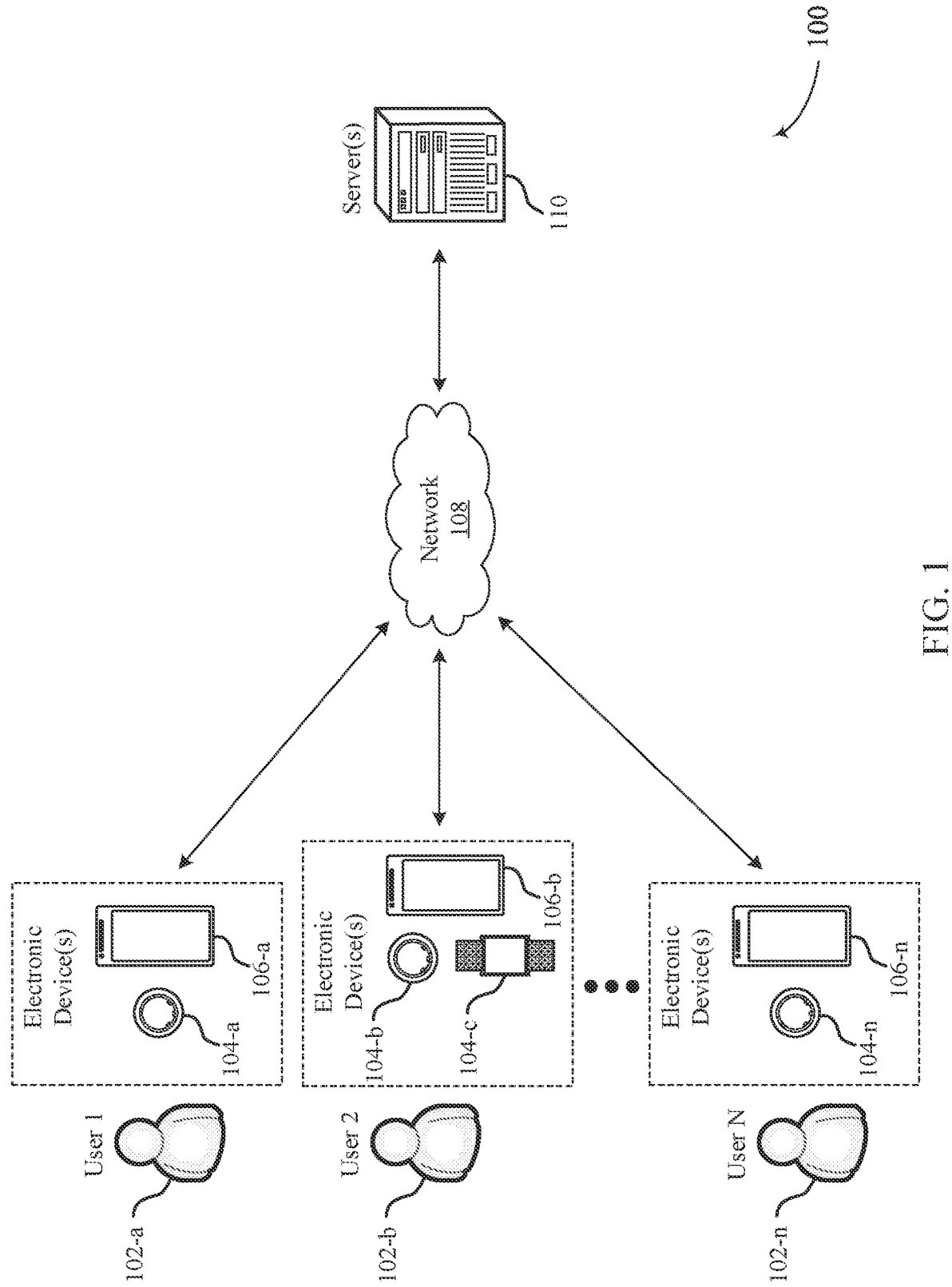
FIG. 1 illustrates an example of a system that supports a universal charger in accordance with aspects of the present disclosure.

Some wearable devices may be configured to collect data from users associated with movement and other activities. For example, some wearable devices may be configured to continuously acquire physiological data associated with a user including temperature data, heart rate data, and the like. In order to efficiently and accurately track physiological data, a wearable device may be configured to collect data continuously while the user wears the device. The wearable device may include a battery or other internal power source, where the wearable device is configured to couple with a charger device which charges the battery or internal power source of the wearable device. However, some conventional charging devices for wearable devices are deficient in that they are expensive to manufacture, and are capable of charging only a limited range of wearable devices (e.g., a charger may only fit a specific size of wearable device).

In some cases, each user may personalize the fit of a wearable device. For example, the user may select a size of a wearable device based on comfort, to maintain skin contact for the sensors to collect the physiological data, or for other reasons. Thus, the size of the wearable device may vary to cover respective variations in user fit (e.g., there may be 5-10 different sizes of a wearable device manufactured). In some examples, the wearable device may come with a charger manufactured for the size of the wearable device. That is, the charger may be specific to the user's wearable device. However, manufacturing multiple chargers (e.g., one for each size ring, or one to cover a range in ring size, such as one or two sizes) may be expensive, and the charger may still have poor contact with the charging coils of the charging device if the charger is manufactured for a range in ring size. Similarly, the wearable device may come with a charger that is relatively large for the wearable device fit, which may cause poor contact with the charging coils of the charging device. These issues may result in the wearable device failing to charge, or charging at a relatively slow speed, and may also incur unnecessary cost related to manufacturing the charging devices.

Accordingly, techniques described herein are directed to systems and methods for charging a wearable device with a universal charger. More specifically, techniques described herein are directed to the use of a magnetic component of a base of a charging device to magnetically attract a magnetic component of the wearable device. The magnets within the wearable device and charging device may orient the wearable device in a radial orientation which allows for a charging process (e.g., to align charging coils at the wearable device and charging device). In some aspects, universal charging devices described herein may be configured to interface with (e.g., charge) wearable devices of varying size. By using magnets to align respective inductive charging components of the charging device and wearable device, techniques described herein may lead to more effective charging for a wearable device (e.g., faster charging, stronger charge signal, reduced or eliminated charging errors, and the like), and may decrease a manufacturing cost of the charging device.

As described herein, a base of the charging device may include a support component (e.g., "support") with an adjustable width, radius, circumference, or any combination thereof. For example, the support may be conical or may otherwise include a taper (e.g., variable circumference) to accommodate multiple sized wearable devices. The wearable device may partially or fully surround the support while the wearable device interfaces with the charging device for charging. For example, a ring, watch, or bracelet may slide onto a conical support to a point where a threshold distance between the device and the support is reached for charging (e.g., wearable device is close enough for wireless charging). One or more magnets within the wearable device and the support may orient the wearable device to a charging position with inductive charging coils aligned for the wearable device and the charging device.

In some examples, the base of a charging device may be a sleeve in which the wearable device may be inserted for charging. A magnetic force may ensure the wearable device remains within the sleeve for charging. For example, a magnetic force may keep the wearable device within the sleeve and may orient the wearable device into a charging position with inductive charging coils aligned for the wearable device and the charging device. In some other examples, the base of a charging component may be a surface, such as a flat surface, a surface with an indent, or both, with one or more magnets positioned beneath the surface. A magnet in the wearable device and the magnets beneath the surface may provide a force to orient the wearable device for charging. For example, the magnets may position the wearable device perpendicular to the surface to align inductive charging coils for the wearable device and the charging device. Additionally or alternatively, the magnets may ensure the wearable device remains in contact with the charging device.

Aspects of the disclosure are initially described in the context of systems supporting physiological data collection from users via wearable devices. Additional aspects of the disclosure are described in the context of charging diagrams. Aspects of the disclosure are further illustrated by and described with reference to apparatus diagrams, system diagrams, and flowcharts that relate to a universal charger.

FIG. 1 illustrates an example of a system 100 that supports a universal charger in accordance with aspects of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices which utilize LEDs which are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time during which the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as sleep scores, readiness scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for a charging device which may charge wearable devices 104 of multiple sizes, shapes, or both. In some cases, a user 102 may purchase a wearable device 104 that has a personalized size. For example, user 102-a may select wearable device 104-a that may be a first size, while user 102-b may select a wearable device 104-b that may be a second size different from the first size. In some cases, a charging device may be manufactured according to the size of each respective wearable device 104. Thus, user 102-a may receive a different charging device than user 102-b. However, if user 102-a attempts to use the charging device of user 102-b, the charging device may not accommodate the size of wearable device 104-a (e.g., because the charging device was manufactured for wearable device 104-b, which may be a different size).

Accordingly, in some aspects, aspects of the present disclosure are directed to universal charging devices which may be configured to charge wearable devices 104 of varying sizes and/or shapes. Universal charging devices described herein may exhibit differing configurations and structural components to interface with wearable deivces 104 to facilitate charging. In some examples, a universal charger may include a charging device with a support for the wearable device 104 that varies in width, circumference, radius, or any combination thereof. In additional or alternative cases, a universal charger may be shaped like a sleeve to accommodate multiple sizes of wearable devices 104, or may include a flat surface designed to accommodate multiple sizes of wearable devices 104.

The charging device may include a magnetic component that attracts a magnetic component on/within a wearable device 104. A magnetic force between the charging components of the wearable device 104 and the charging device may orient the wearable device 104 in a charging position (e.g., a position which facilitates charging). For example, the wearable device 104 may stand perpendicular to a surface of the charging device, remain within a recess of a sleeve of the charging device, or may sit on a support of the charging device, such that an inductive charging component of the charging device aligns with an inductive charging component of the wearable device 104. In some examples, the magnetic component in the wearable device 104, the charging device, or both may include a rare earth magnet or other manufactured or naturally occurring magnet. In some other examples, the magnetic components may be charging coils that create a magnetic force in proximity of each other.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
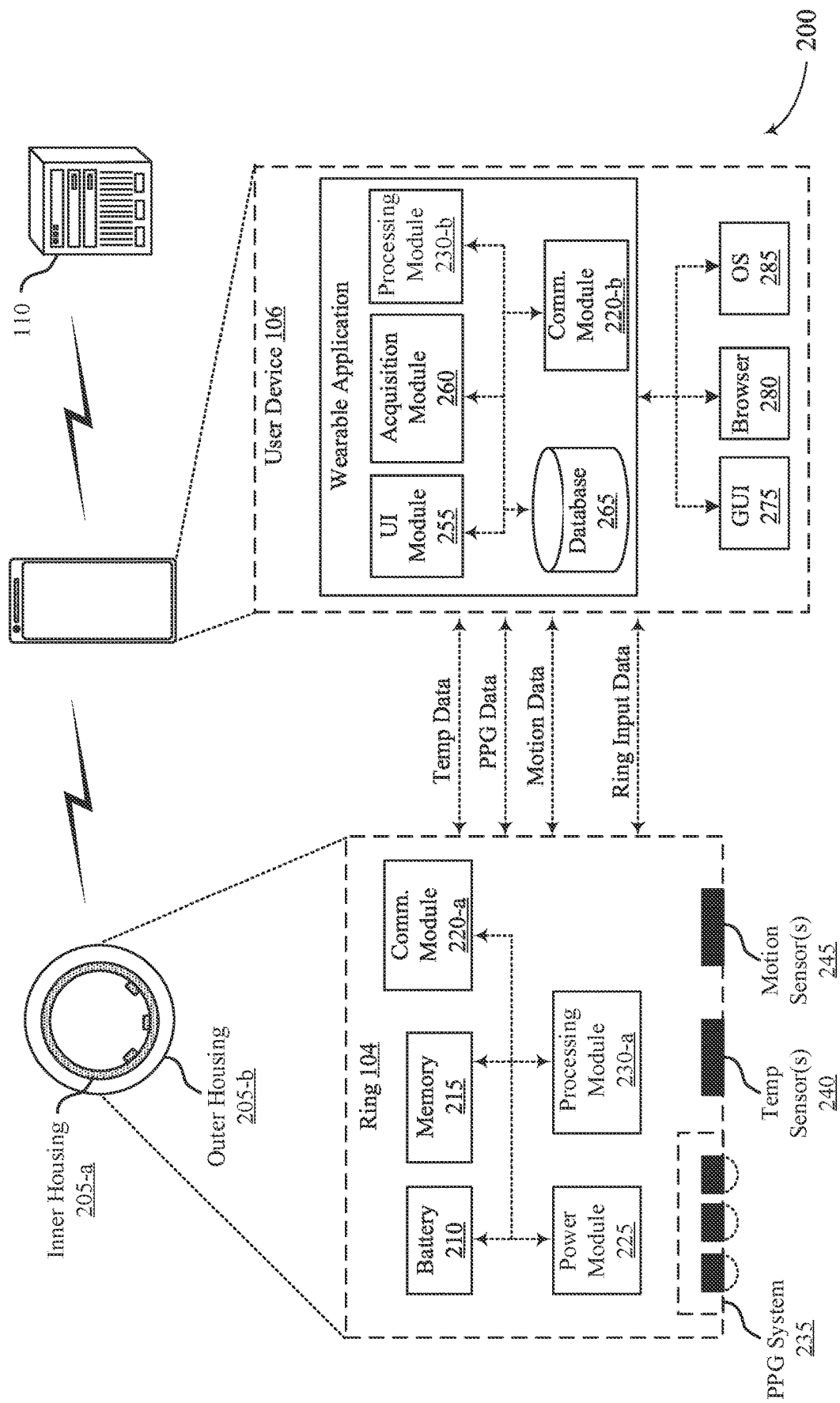
FIGS. 2 and 3 illustrate examples of systems that support a universal charger in accordance with aspects of the present disclosure.

FIG. 2 illustrates an example of a system 200 that supports a universal charger in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers.

As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMl160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a sleep score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations which require relatively low processing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., sleep score, readiness score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, sleep scores, readiness scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., sleep score, readiness score) may be determined/calculated based on one or more "contributors," "factors," or "contributing factors." For example, a user's overall sleep score may be calculated based on a set of contributors, including: total sleep, efficiency, restfulness, REM sleep, deep sleep, latency, timing, or any combination thereof. The sleep score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall readiness score may be calculated based on a set of contributors, including: sleep, sleep balance, heart rate, HRV balance, recovery index, temperature, activity, activity balance, or any combination thereof. The readiness score may include any quantity of contributors. The "sleep" contributor may refer to the combined sleep score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the readiness score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for a universal charger to charge a wearable device or ring 104. The universal charger may be a charging device with a support for the wearable device 104 that varies in width, circumference, radius, or any combination thereof. In additional or alternative implementations, the universal charger may be shaped like a sleeve to accommodate multiple sizes of wearable devices 104, or may include a flat surface designed to accommodate multiple sizes of wearable devices 104. The charging device may include a magnetic component that attracts a magnetic component on a wearable device 104. A magnetic force between the magnetic components of the charging device and the wearable device 104 may orient the wearable device 104 in a charging position relative to the charging device. For example, the wearable device 104 may stand perpendicular to the surface, remain at the base of a sleeve, or may sit on the support, such that an inductive charging component of the charging device aligns with an inductive charging component of the wearable device 104. For the purposes of the present disclosure, the term "charging position," and like terms, may refer to a position or orientation of the wearable device 104 relative to the charging device which facilitates or enables charging of the wireless device 104.

In some cases, the charging position may be based on a threshold distance between the wearable device 104 and the charging device (e.g., may satisfy a threshold distance, such as by being below the threshold). For example, the charging position may orient the inductive charging component of the wearable device 104 (e.g., receiver coil) within a threshold distance of the inductive charging component of the charging device (e.g., transmitter coil) to facilitate wireless charging of the wearable device 104. If the charging device includes a support for the wearable device, the threshold distance may be between inner housing 205-a and the outer surface of the support. If the charging device is a sleeve or flat surface, the threshold distance may be between outer housing 206-a and the outer surface of the surface or inside the sleeve. In some aspects, the threshold distance may be based on parameters of the magnetic components of the wearable device 104 and/or the charging device, inductive components of the wearable device 104 and/or the charging device, or any combination thereof. For example, the threshold distance for wireless charging may be based on a strength/type of the magnetic components, a strength/type/efficiency of the inductive components, and the like.

Figure 3:
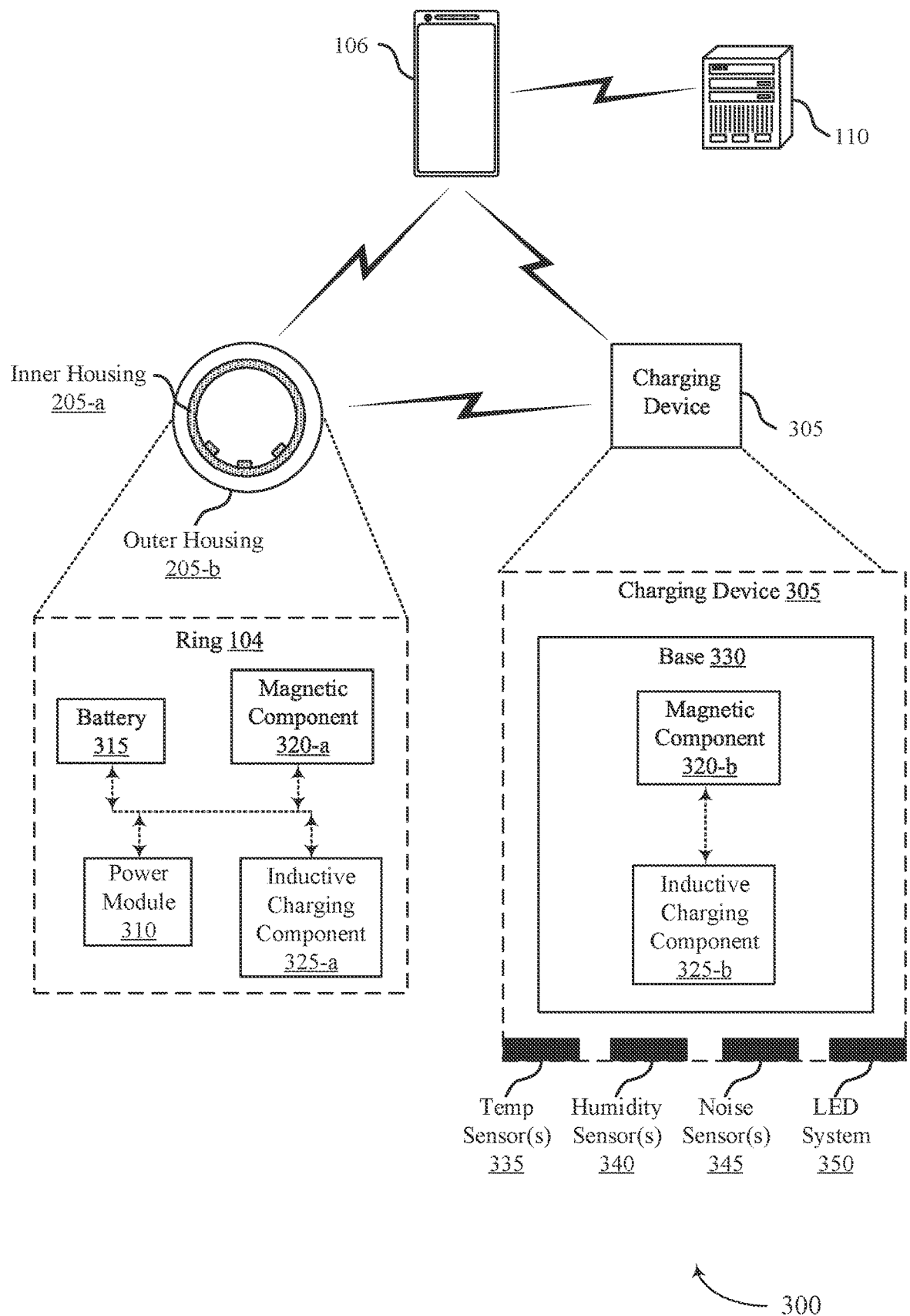

FIG. 3 illustrates an example of a system 300 that supports a universal charger in accordance with aspects of the present disclosure. The system 300 may implement, or be implemented by, system 100, system 200, or both. In particular, system 300 illustrates an example of a ring 104 (e.g., wearable device 104), as described with reference to FIG. 1, and a charging device 305.

In some aspects, the ring 104 may be configured to be worn around a user's finger, and may measure one or more user physiological parameters when worn around the user's finger. Example measurements and determinations may include, but are not limited to, user skin temperature, pulse waveforms, respiratory rate, heart rate, HRV, blood oxygen levels, and the like.

System 300 further includes a charging device 305 in communication with the ring or with a user device 106, as described with reference to FIG. 2. The ring 104 may be in wireless and/or wired communication with a user device 106 and/or server 110. Similarly, the charging device 305 may be in wireless and/or wired communication with a user device 106, the ring 104, a server 110, or any combination thereof. In some implementations, the charging device 305 may send measured and processed data (e.g., temperature data, humidity data, noise data, and the like) to the user device 106, the ring 104, or both. Various data processing procedures described herein may be performed by any of the components of system 300, including the ring 104, charging device 305, user device 106, server 110, or any combination thereof.

Data may be collected and analyzed via one or more components of the system 300. Moreover, in some implementations, the charging device 305 may be configured to collect and analyze data, including ambient temperature data, noise data, and the like. For example, the user device 106 may determine a correlation between sleep data from the ring 104 and the measured and processed data from the charging device 305 (e.g., if the air temperature is relatively high, a user of the ring 104 may wake up throughout a sleep duration). In other words, data collected via the charging device 305 (e.g., ambient air temperature data, noise data) may be used to further analyze physiological data collected via the ring 104.

The ring 104 may include an inner housing 205-a and an outer housing 205-b, as described with reference to FIG. 2. In some aspects, the housing 205 of the ring 104 may store or otherwise include various components of the ring 104 including, but not limited to, device electronics (e.g., a power module 310, which may be an example of a power module 225 as described with reference to FIG. 2), a power source (e.g., battery 315, which may be an example of a battery 210 as described with reference to FIG. 2, and/or capacitor), one or more substrates (e.g., printable circuit boards) that interconnect the device electronics and/or power source, and the like. In some examples, the housing 205 may also store a magnetic component 320-a (e.g., ferrite tape, other charging magnet, a transmitter coil, a rare earth magnet, or the like) and an inductive charging component 325 (e.g., inductive charging component 325-a).

The ring 104 shown and described with reference to FIGS. 2 and 3 is provided solely for illustrative purposes. As such, the ring 104 may include additional or alternative components as those illustrated in FIGS. 2 and 3. Other rings 104 that provide functionality described herein may be fabricated. For example, rings 104 with fewer components (e.g., sensors) may be fabricated. In a specific example, a ring 104 may include ferrite tape, which may act as both the magnetic component 320-a and the inductive charging component 325-a. In other cases, the ring 104 may include a dedicated charger magnet. For example, the ring 104 may include a metal plate and/or ferrite tape disposed proximate to a charger magnet.

In some examples, the ring 104 may be in electronic communication with the charging device 305. The charging device 305 may charge the battery 315 of the ring 104. The charging device 305 may include a base 330, which may store or otherwise include various components of the charging device 305. In some aspects, the base 330 of the charging device 305 may store or otherwise include various components of the charging device 305 including, but not limited to, a magnetic component 320-b (e.g., ferrite tape, a transmitter coil, a rare earth magnet, or the like) and an inductive charging component 325-b.

In some cases, the magnetic component 320-b of the base 330 may include multiple magnets arranged according to a pattern based on a polarity of each magnet. For example, each magnet may have a polarity facing outward towards the surface of the charging device 305 to attract the magnetic component 320-a of the ring 104 with an opposite polarity. The inductive charging component 325-b of the charging device 305 (e.g., transmitter coil, ferrite tape) may couple with inductive charging component 325-a of the ring 104 (e.g., receiver coil, ferrite tape) to charge the battery 315 of the ring 104. Inductive charging may also be referred to as wireless charging, and may allow power to transfer from the charging device 305 to the battery 315 of the ring 104 using electromagnetic induction. Although the charging device 305 and the ring 104 are illustrated as including inductive charging components 325, the charging device 305 and the ring 104 may include any type of charging components, such as wired charging components.

In some examples, the charging device 305 may include one or more temperature sensors 335. The temperature sensors 335 may measure an average air temperature over a duration, may continuously measure air temperature, or both. Similarly, the charging device 305 may include one or more humidity sensors 340. The humidity sensors 340 may measure an average humidity level over a duration, may continuously measure humidity level, or both. The humidity sensors 340 may measure the humidity as a percentage (e.g., 35% humidity). The charging device 305 may include one or more noise sensors 345. The noise sensors 345 may measure a noise level (e.g., in decibels) averaged over a duration, continuously, or both. The charging device 305 may store the humidity measurements, the temperature measurements, the noise measurements, or a combination thereof.

The charging device 305 may include any type of sensor known in the art, and may be configured to collect any type of data which may be used to provide insight into a user's environment and overall health. For example, the charging device 305 may include light sensors configured to measure an amount of light and/or type of light (e.g., wavelength). In such cases, the system 300 may be configured to determine whether light levels and/or which types of light may result positively or negatively affect a user's sleep and health (e.g., determine if blue light is more disruptive to a user's sleep as compared to red light). By way of another example, the charging device may include air quality sensors configured to measure air quality, pollutants, allergens, and the like. Data collected via sensors of the charging device may be leveraged to determine how a user's surrounding environment may affect their physiological data, sleep, and overall health. A processing module, such as a processing module 230 as described with reference to FIG. 2, at the user device 106 or at the charging device 305 may process the data from the temperature sensors 335, the humidity sensors 340, the noise sensors 345, light sensors, air quality sensors, or a combination thereof.

In some examples, the user device 106 and/or charging device 305 may process the data from the temperature sensors 335, the humidity sensors 340, the noise sensors 345, or a combination thereof in conjunction with data from the ring 104. For example, the user device 106 may receive physiological data collected by the ring 104 which reflects one or more sleep cycles of a user, and may use the data from the sensors at the charging device 305 to determine a correlation between the collected physiological data and data collected by the charging device 305. For example, the user device 106 may determine a correlation over a time interval between data collected by the charging device 305 (e.g., ambient temperature data, humidity data, noise data, and the like) with a quality of sleep for the user (as determined by collected physiological data). In other words, the system 300 may be configured to identify whether high/low temperature, humidity, and/or noise levels result in a disruption of the user's sleep cycles (e.g., low ambient temperature and humidity levels result in higher quality sleep, higher noise levels result in lower quality sleep).

Although the charging device 305 is illustrated as including temperature sensors 335, humidity sensors 340, and noise sensors 345, the charging device 305 may include any number and type of sensors in one or more locations. For example, the charging device may also include a motion sensor, a light sensor, or the like.

In some cases, the charging device 305 may include an LED system 350. The LED system 350 may display one or more indications to a user of the ring 104. For example, the LED system 350 may display a battery level of the battery 315, a battery health/charge status (e.g., end of battery life), a time of day, connectivity issues, one or more scores of the user (e.g., a sleep score related to how well a user slept, a readiness score or level, an activity level, or the like). Additionally or alternatively, the LED system 350 may display one or more alerts to the user (e.g., action items prompting the user to perform an action, and the like). The LED system 350 may display a battery level of the battery 315 of the ring 104 as a percentage of total battery by displaying the numbers of the percentage, by illuminating a portion of LEDs (e.g., if a battery level is at 50%, 5 of 10 LEDs may be displayed), or the like. The LEDs in the LED system 350 may be oriented in any arrangement on the charging device 305, may be any color combination (e.g., red LED, blue LED, green LED), and there may be any number of LEDs in the LED system 350.

In some implementations, the charging device 305 may include a wired or wireless power source. For example, in some cases, the charging device 305 may be coupled to an electrical outlet or other power source. In other cases, the charging device 305 may include a battery or other internal power source to enable mobile charging of the ring 104. For example, in some implementations, the charging device 305 may include a battery or other internal power source such that a user may physically wear or carry the charger along with the ring 104 for mobile charging. For instance, the charger device 305 may be worn on a necklace so that a user may wear the charger while simultaneously charging the ring 104. In other cases, the charger 305 may be coupled to the ring 104 (e.g., magnetically coupled, mechanically snapped onto) the ring 104 while the ring 104 is being worn so that the ring 104 may be charged (and continue to collect physiological data) as it is worn.

Figure 4:
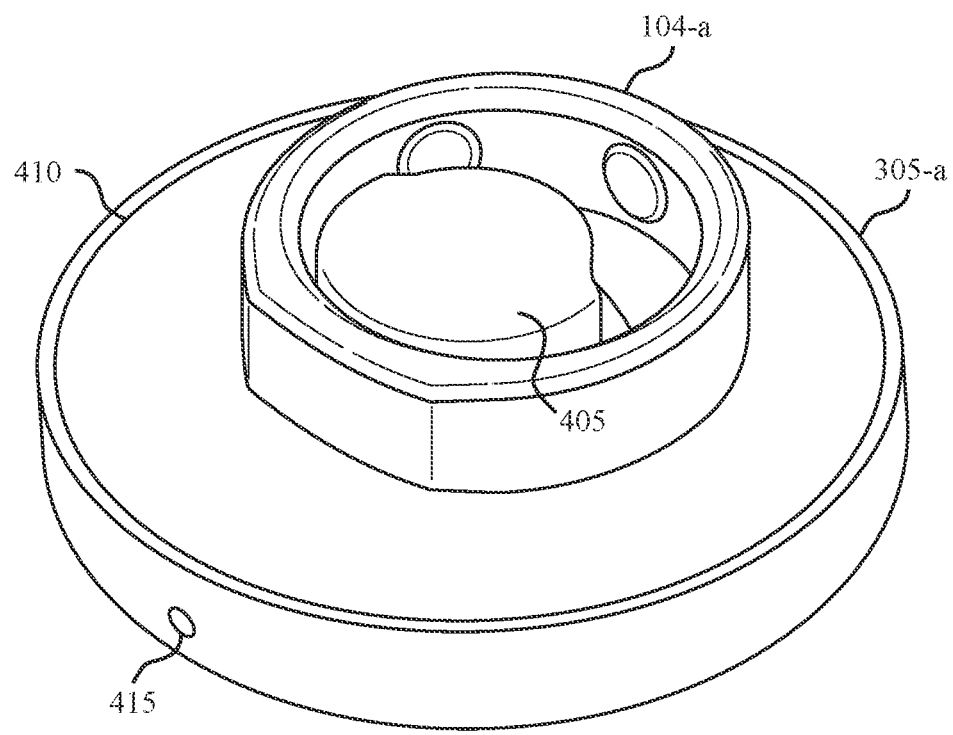
FIGS. 4-9 illustrate examples of charging diagrams that support a universal charger in accordance with aspects of the present disclosure.

FIG. 4 illustrates an example of a charging diagram 400 that supports a universal charger in accordance with aspects of the present disclosure. The charging diagram 400 may implement, or be implemented by, aspects of the system 100, system 200, system 300, or a combination thereof. For example, charging diagram 400 may illustrate examples of a wearable device 104-a and a charging device 305-a, which may be examples of a wearable device 104 and a charging device 305 as described with reference to FIG. 3. Specifically, the charging diagram 400 may illustrate use of a magnetic force to orient wearable device 104-a in a charging position. Although wearable device 104-a is illustrated as a ring in FIG. 4, wearable device 104-a may be any example of a wearable device 104 (e.g., a watch, necklace, bracelet, and the like).

In some examples, charging diagram 400 may include a charging device 305, such as charging device 305-a, which may charge the wearable device 104-a. The charging device 305-a may include a base 410 and a support 405. The charging device 305-a may be manufactured according to an inner diameter of the wearable device 104-a. Moreover, the charging device 305-a may be manufactured to provide wireless charging to wearable devices 104-a of multiple sizes. In this regard, a circumference and/or diameter of the support 405 may be manufactured such that an inner diameter of a smallest wearable device 104-a is larger than the circumference/diameter of the support 305. Additionally, the charging device 305-*a* may be manufactured such that a threshold distance between the inner surface of the wearable device 104 and a support 405 connected to the base 410 of the charging device 305 is below a threshold. The threshold distance may be determined based on a distance for wireless charging (e.g., where one or more inductive charging components of the wearable device 104-*a* are within a threshold distance of inductive charging components of the charging device 305-*a* to induce current to charge the wearable device 104-*a*). However, manufacturing different size or shape supports 405 based on a size and shape of a wearable device 104 may incur unnecessary cost.

Thus, charging device 305-*a* may include a magnetic component to magnetically attract a magnetic component in wearable device 104-*a*, as shown and described in FIG. 3. For example, a support 405 of charging device 305-*a* may include a magnet (e.g., a rare earth magnet, ferrite tape, a transmitter coil, or the like), and wearable device 104-*a* may include a similar magnet. The magnets or magnetic components may create a magnetic force to orient the wearable device 104-*a* in a charging position and to ensure a charging component of wearable device 104-*a* remains within a threshold distance of charging components of charging device 305-*a* located within the support 405. The location and function of the magnetic and inductive components of the wearable device 104-*a* and charging device 305-*a* are described in further detail with respect to FIG. 5.

In some examples, charging device 305-*a* may include an LED 415 to display a charging status. For example, the LED 415 may blink while wearable device 104-*a* is actively charging, and may turn solid when wearable device 104-*a* has reached a maximum or threshold charge. In some cases, the LED 415 may indicate one or more alerts to the user (e.g., by changing colors, blinking, flashing, etc.). For example, the LED 415 may turn red if there is a charging malfunction (e.g., connectivity issues), or the like. In some cases, the support 405 may be capable of charging multiple wearable devices 104. The LED 415 may indicate which of the multiple rings or other wearable devices may be charged using different colors or flashing patterns.

In some examples, charging device 305-*a* may be a universal charger. That is, charging device 305-*a* may accommodate each manufactured size wearable device 104-*a*. The support 405 may be manufactured to fit a wearable device 104 with a smallest size. The support 405 may be any size or shape, such as conical, cylindrical, square, and the like, which is described in further detail with respect to FIG. 6.

Figure 5:
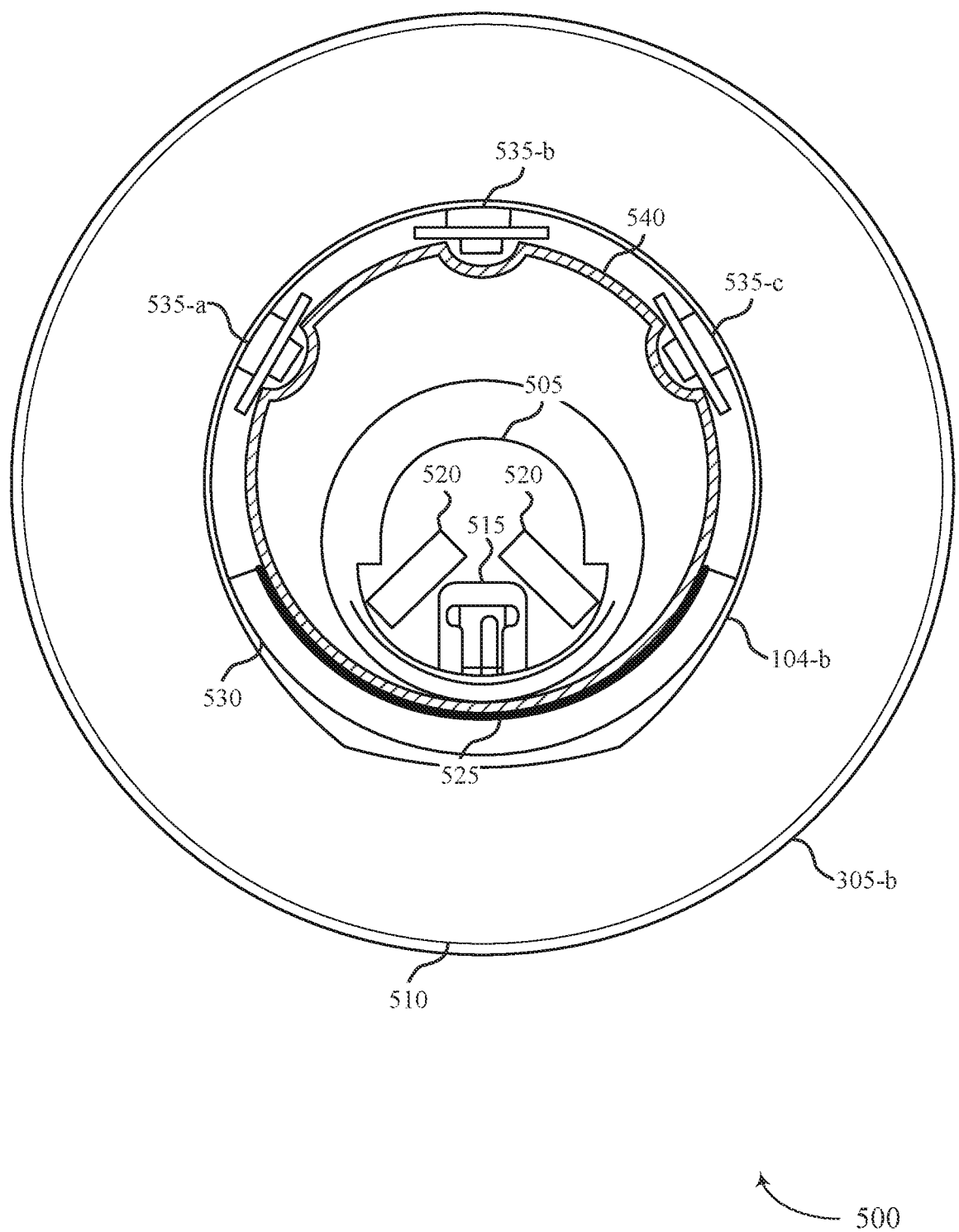

FIG. 5 illustrates an example of a charging diagram 500 that supports a universal charger in accordance with aspects of the present disclosure. The charging diagram 500 may implement, or be implemented by, aspects of the system 100, system 200, system 300, charging diagram 400, or any combination thereof. For example, charging diagram 500 may illustrate examples of a wearable device 104-*b* and a charging device 305-*b*, which may be examples of wearable devices 104 and charging devices 305 as described with reference to FIGS. 3-4. Specifically, the charging diagram 500 may illustrate components for use of a magnetic force to orient wearable device 104-*b* in a charging position. Although wearable device 104-*b* is illustrated as a ring in FIG. 5, wearable device 104-*b* may be any example of a wearable device 104 (e.g., a watch, necklace, bracelet, and the like).

In some examples, charging diagram 500 may include a charging device 305, such as charging device 305-*b*, which may charge the wearable device 104-*b*. Charging device 305-*b* may include a support 505, which may be connected to a base 510 of charging device 305-*b*. The support 505 may include one or more inductive charging components 515. The inductive charging components 515 may include components which facilitate wireless charging, including, but not limited to, a charging coil (e.g., transmitter coil), ferrite tape, and the like. In some cases, charging device 305-*b* may include one or more magnetic components 520. The magnetic components 520 may include rare earth magnets, or other magnetic materials. The magnetic component 520 may be positioned within the support 505.

In some implementations, the magnetic component 520 may wrap around the front of the support 505. In some cases, the magnetic component 520 of charging device 305-*b* may attract a magnetic component 525 of wearable device 104-*b* in order to orient the wearable device 104-*b* in a charging position. The magnetic component 525 of the wearable device 104-*b* may be ferrite tape, a charger magnet, a transmitter coil, or any combination thereof. For example, in some implementations, the magnetic component 525 may include a metal plate and ferrite tape disposed against a charger magnet which is configured to magnetically interact with the magnetic components 820 of the charging device 305-*g*. The magnetic component 525 (e.g., ferrite tape, charger magnet) may be used for wireless charging. In some aspects, the wearable device 104-*b* may be positioned around the support 505 in any number of radial orientations, where a single radial orientation includes a charging position for the wearable device 104-*b*. In such cases, the single radial orientation may position the inductive charging component 515 of the charging device 305-*b* within a threshold distance of an inductive charging component of the wearable device 104-*b* to enable wireless charging (e.g., inductive charging). In other words, the wearable device 104-*b* may be oriented in a defined radial position on the charging device 305-*b* in order to facilitate wireless charging.

Due to the magnetic qualities of ferrite, the ferrite tape may also act as the magnetic component 525 to orient wearable device 104-*b* in a charging position favorable for wireless charging. In other words, ferrite tape within the wearable device 104-*b* may serve as the magnetic component 525 of the wearable device 104-*b*, the inductive component of the wearable device 104-*b*, or both. For example, a magnetic force may attract the magnetic component 525 (e.g., ferrite tape, other charger magnet) and the magnetic component 520 to reduce a threshold distance between the inductive charging components 515 of charging device 305-*b* and one or more inductive charging components of the wearable device 104-*b* to facilitate wireless charging of the wearable device 104-*b*. In some aspects, inductive components of the wearable device 104-*b* may be located in a PCB 530. In some examples, the wearable device 104-*b* may include a PCB 530 that includes or otherwise connects one or more charging coils, a battery, one or more sensors 535, and a processor.

In some examples, one or more wires 540 or other conductive components may connect sensors 535 (e.g., sensors used for collecting physiological data of a user) to PCB 530, which may include a logic board for wearable device 104-*b*. For example, the wires 540 may connect sensor 535-*a*, sensor 535-*b*, and sensor 535-*c* to PCB 530. The magnetic component 525 may be located at the front, or top, of wearable device 104-*b*. The magnetic component 525 may span a portion, or multiple portions, of the inner surface of wearable device 104-*b*. For example, the magnetic component 525 may be positioned to orient wearable device 104-*b* to a correct position (e.g., charging position) for charging regardless of an orientation of wearable device 104-*b*.

In some examples the magnetic component 520 of the support 505 may exert a tangential force on wearable device 104-*b* based on a magnetic force with the magnetic component 525 of the wearable device 104-*b*. The tangential force may arrange wearable device 104-*b* in a radial orientation for wireless charging (e.g., charging position). For example, the tangential force may rotate wearable device 104-*b* clockwise relative to an axis of the support 505 or counterclockwise relative to an axis of the support 505. In particular, the magnetic components 520, 525 may exert a tangential force which orients the wearable device 104-*b* in a defined radial position relative to the charging component 104-*b* for wireless charging. For instance, if the wearable device 104-*b* is placed on the charging component 305-*b* in a non-charging position (e.g., rotated with respect to the charging position), the magnetic components 520, 525 may exert a tangential force which rotates the wearable device 104-*b* into the charging position.

Figure 6A:
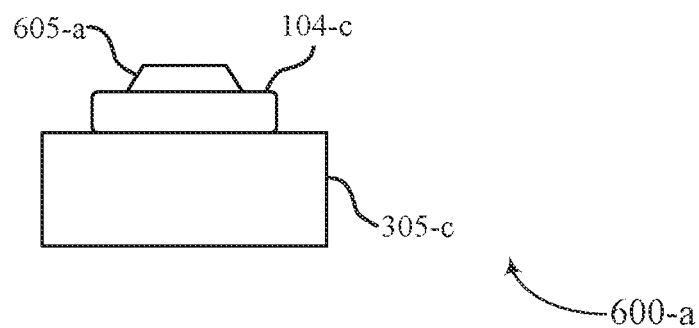
Figure 6B:
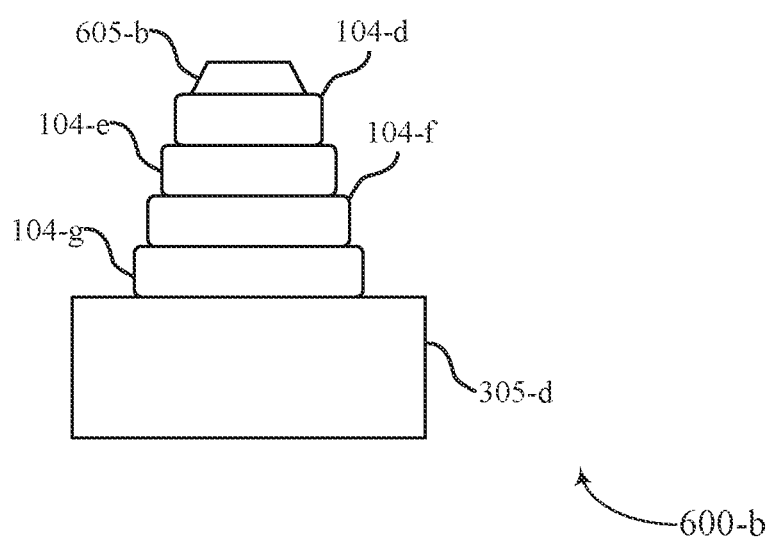
Figure 6C:
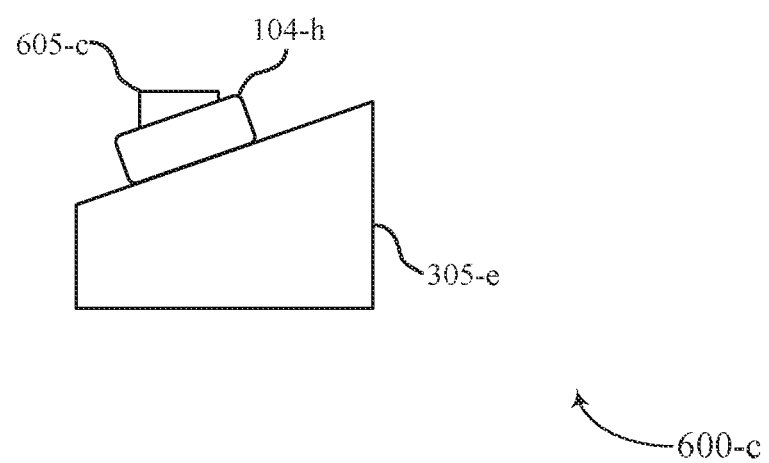

FIGS. 6A, 6B, and 6C illustrates an example of a charging diagram 600 that supports a universal charger in accordance with aspects of the present disclosure. The charging diagram 600 may implement, or be implemented by, aspects of the system 100, system 200, system 300, charging diagram 400, charging diagram 500, or a combination thereof. For example, charging diagram 600-*a*, charging diagram 600-*b*, and charging diagram 600-*c*, may illustrate examples of wearable devices 104 as described with reference to FIGS. 1-5. Specifically, the charging diagram 600-*a*, charging diagram 600-*b*, and charging diagram 600-*c* may illustrate different orientations of a wearable device 104 on a charging device 305 with a support 605. Although the wearable devices are illustrated as rings in FIG. 6, they may be any example of a wearable device (e.g., a watch, a necklace, and the like).

In some examples, charging diagram 600-*a* may include a charging device 305, such as charging device 305-*c*, which may charge one or more wearable devices 104. Charging device 305-*c* may include a support 605-*a*, which may be connected to a base of charging device 305-*c*. The support 605-*a* may include one or more inductive charging components and a magnetic component, as described with reference to FIG. 5. In some cases, the magnetic component of a charging device 305-*c* may attract a magnetic component of a wearable device 104-*c* to orient wearable device 104-*c* in a charging position favorable for wireless charging. For example, a magnetic force may attract the magnetic component of wearable device 104-*c* to a conical support 605-*a* to reduce a threshold distance between the inductive charging components of charging device 305-*c* and one or more inductive charging components wearable device 104-*c*.

A support 605 of a charging device 305 may accommodate one or more wearable devices 104. For example, as illustrated in charging diagram 600-*b*, support 605-*b* of wearable device 305-*d* may be tall enough to fit multiple wearable devices 104, such as wearable device 104-*d*, wearable device 104-*e*, wearable device 104-*f*, wearable device 104-*g*, or a combination thereof. In some cases, a support 605-*b* may vary in diameter, circumference, or both to fit wearable devices 104 of varying sizes. For example, wearable device 104-*d* may have a relatively small inner circumference when compared with wearable device 104-*g*. Support 605-*b* may have a relatively smaller circumference at a top of support 605-*b* and a relatively larger circumference at a bottom of support 605-*b*. Thus, charging device 305-*d* may charge wearable devices 104 of multiple sizes, and may charge them concurrently.

In some examples, a support 605 may be conical, as illustrated with respect to FIGS. 6A and 6B, or may otherwise vary in diameter, circumference, or any other dimension to accommodate one or more wearable devices 104. In some other examples, as illustrated in charging diagram 600-*c*, the support 605-*c* may not vary in diameter or circumference. For example, support 605-*c* of charging device 305-*e* may be cylindrical. The circumference of support 605-*c* may accommodate multiple inner circumferences of wearable devices 104, such as wearable device 104-*h*. In some implementations, the support 605 may be adjustable in width, radius, circumference, or any combination thereof. In this regard, a user may be able to adjust a size of the support 605 in order to facilitate wireless charging of varying sizes of wireless devices 104.

In some cases, the base of charging device 305-*e* may be tilted at an angle, such that gravity may assist in keeping the wearable device 104-*h* in a charging position (e.g., assist with keeping the distance between the inner surface of wearable device 104-*h* and support 605-*c* within a threshold distance for wireless charging). In some other cases, the base of charging device 305-*e* may be level (e.g., flat), and the magnetic force may be sufficient to keep the distance between the inner surface of wearable device 104-*h* and support 605-*c* within the threshold distance.

In some examples, support 605-*c* may be taller to support additional wearable devices 104-*h*, similar to charging diagram 600-*b*. Support 605-*c* may be a cylinder, a square, rectangular, or any other shape that provides for a charging component of wearable device 104-*h* to pair with a charging component of charging device 305-*e*.

Figure 7:
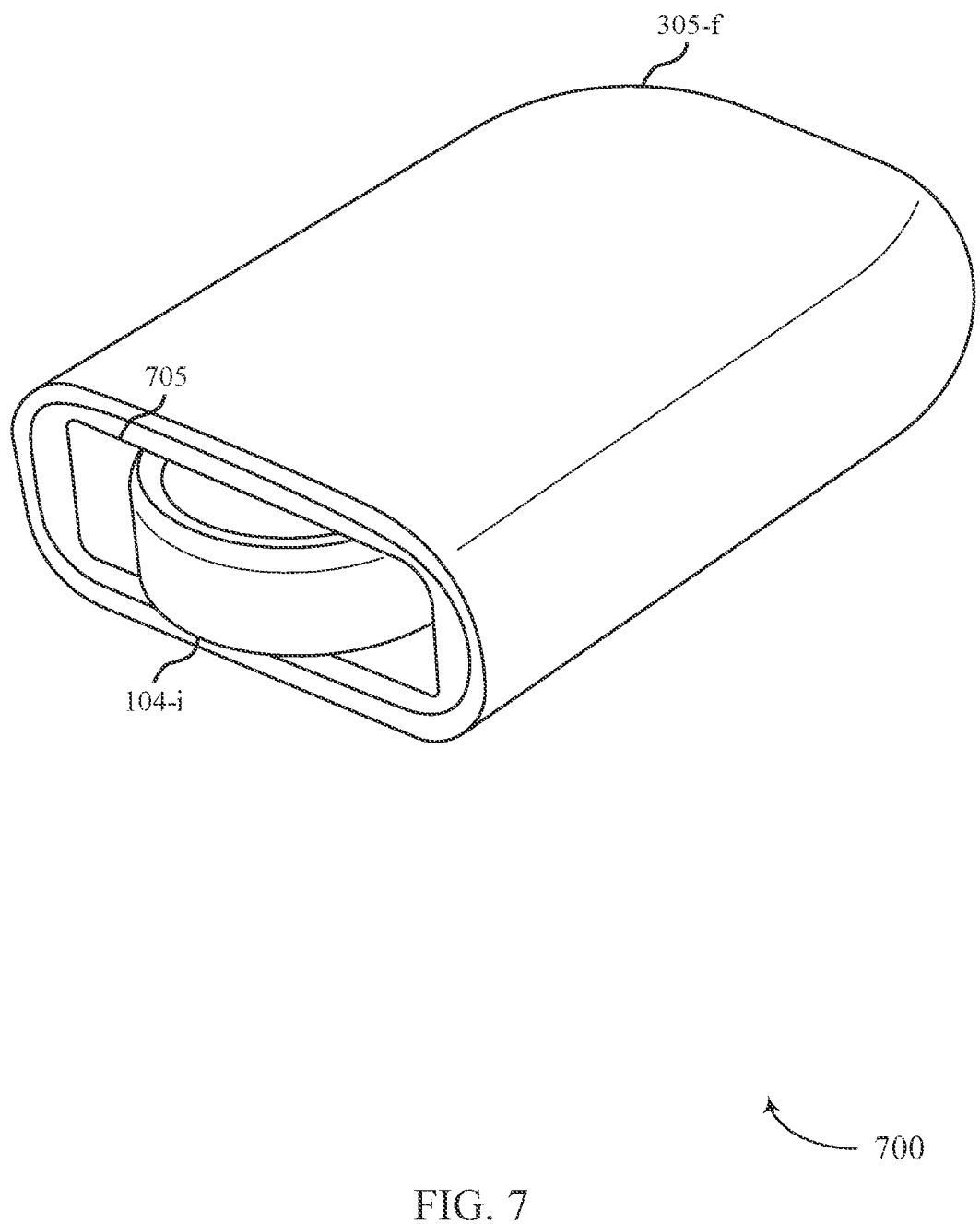

FIG. 7 illustrates an example of a charging diagram 700 that supports a universal charger in accordance with aspects of the present disclosure. The charging diagram 700 may implement, or be implemented by, aspects of the system 100, system 200, system 300, charging diagram 400 through charging diagram 600, or a combination thereof. For example, charging diagram 700 may illustrate examples of a wearable device 104-*i* and a charging device 305-*f*, which may be examples of a wearable device 104 and a charging device 305 as described with reference to FIGS. 3-6. Specifically, the charging diagram 700 may illustrate use of a magnetic force to orient wearable device 104-*i* in a charging position. Although wearable device 104-*i* is illustrated as a ring in FIG. 7, wearable device 104-*i* may be any example of a wearable device 104 (e.g., a watch, necklace, bracelet, and the like).

In some examples, charging diagram 700 may include a charging device 305, such as charging device 305-*f*, which may charge a wearable device 104. Charging device 305-*f* may include a magnetic component to magnetically attract a magnetic component in wearable device 104-*i*. For example, a sleeve 705 of charging device 305-*a* may include a magnet (e.g., a rare earth magnet, ferrite tape, a transmitter coil, or the like) within the sleeve 705 (e.g., at a bottom of the sleeve 705), and wearable device 104-*i* may include a similar magnet. The magnets or magnetic components may create a magnetic force to ensure a charging component (e.g., inductive component) of wearable device 104-*i* remains within a threshold distance of charging components of charging device 305-*f* located within the sleeve 705 to facilitate wireless charging. The location and function of the magnetic components are described in further detail with respect to FIG. 8.

In some examples, charging device 305-*f* may include an LED to display a charging status. For example, the LED may blink while wearable device 104-*i* is actively charging, and may turn solid when wearable device 104-*i* has reached a maximum or threshold charge. In some cases, the LED may indicate one or more alerts to the user (e.g., by changing colors). For example, the LED may turn red if there is a charging malfunction, or the like. In some cases, the sleeve 705 may be capable of charging multiple wearable devices 104. The LED may indicate using different colors or flashing patterns which of the multiple rings may be charged.

In some examples, charging device 305-*f* may be a universal charger which supports wireless charging of various sizes of wearable devices 104. That is, charging device 305-*f* may accommodate each manufactured size wearable device 104-*i*. An opening of the sleeve 705 may be manufactured to fit a wearable device 104 with a largest size, such that the sleeve 705 is configured to receive the wearable device 104 with the largest size as well as smaller wearable devices 104. The sleeve 705 may be any size or shape, such as conical, cylindrical, square, and the like to accommodate the wearable devices 104. In some aspects, the sleeve 707 may be configured to receive the wearable device 104-*i* for wireless charging, where the sleeve 705 is configured to at least partially surround the wearable device 104-*i* while the wearable device 104-*i* is in the charging position.

Figure 8:
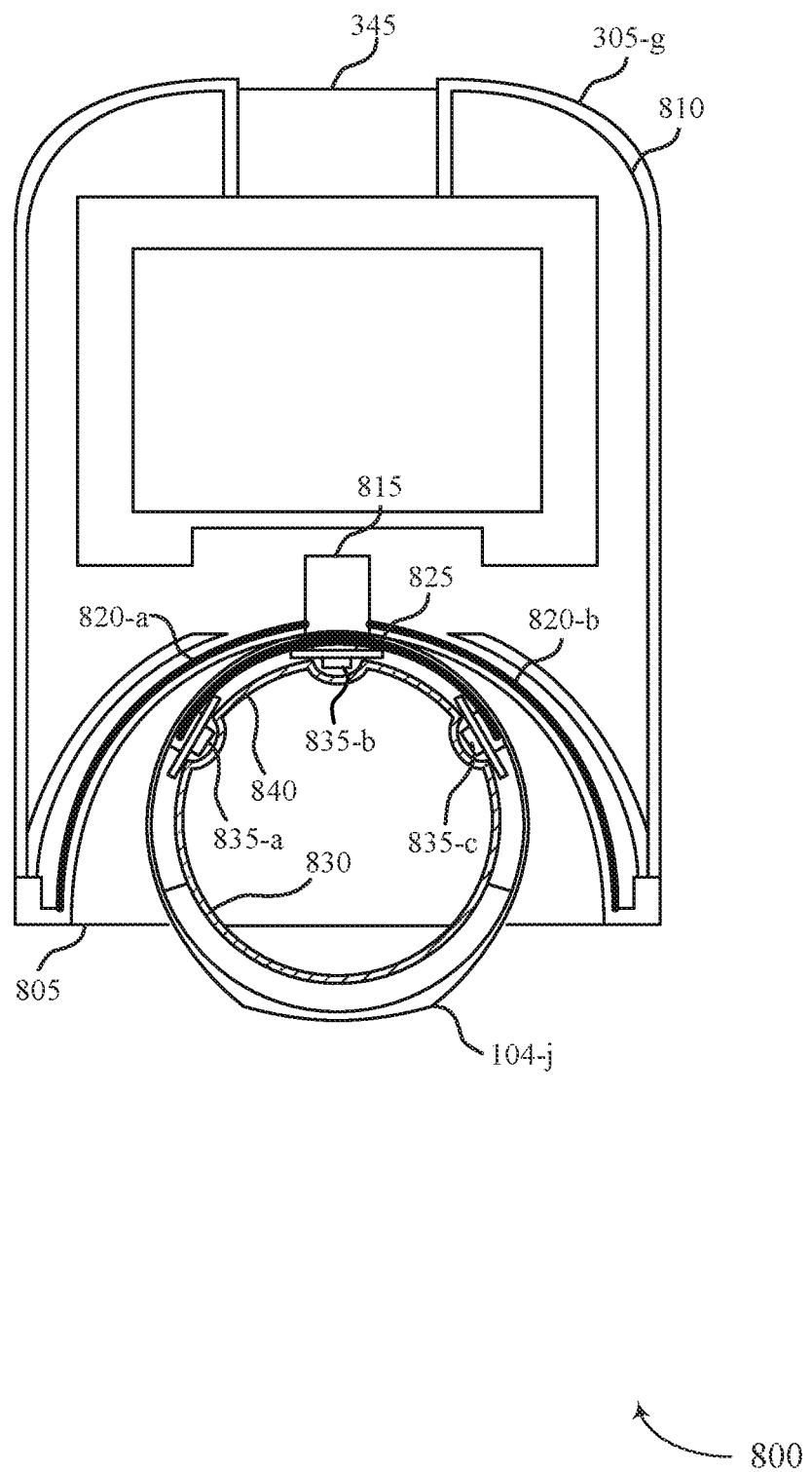

FIG. 8 illustrates an example of a charging diagram 800 that supports a universal charger in accordance with aspects of the present disclosure. The charging diagram 800 may implement, or be implemented by, aspects of the system 100, system 200, system 300, charging diagram 400 through charging diagram 700, or a combination thereof. For example, charging diagram 800 may illustrate examples of a wearable device 104-*j* and a charging device 305-*g*, which may be examples of a wearable device 104 and a charging device 305 as described with reference to FIG. 3-7. Specifically, the charging diagram 800 may illustrate components which utilize a magnetic force to orient wearable device 104-*j* in a charging position. Although wearable device 104-*j* is illustrated as a ring in FIG. 8, wearable device 104-*j* may be any example of a wearable device 104 (e.g., a watch, necklace, bracelet, and the like).

In some examples, charging diagram 800 may include a charging device 305, such as charging device 305-*g*, which may charge a wearable device 104. Charging device 305-*g* may include a sleeve 805, which may be within a base 810 of charging device 305-*g*. The base 810 may include one or more inductive charging components 815. The inductive charging components 815 may include any components configured to facilitate wired or wireless charging including, but not limited to, a charging coil (e.g., transmitter coil), ferrite tape, and the like. In some cases, charging device 305-*g* may include one or more magnetic components 820, such as magnetic component 820-*a* and magnetic component 820-*b*. The magnetic components 820 may be rare earth magnets, ferrite tape, a transmitter coil, or other magnetic material. The magnetic components 820 may wrap around the inside of the sleeve 805 (e.g., around interior surfaces of the sleeve 805). For example, the sleeve 805 may include magnetic component 820-*a* around one side of the sleeve 805 and magnetic component 820-*b* around the other side of the sleeve 805. In some cases, the magnetic components 820 of charging device 305-*g* may attract a magnetic component 825 of wearable device 104-*j*. In some implementations, the magnetic component 825 may include ferrite tape. Additionally, or alternatively, the magnetic component 825 may include a charger magnet configured to magnetically interact with the magnetic components 820 of the charging device 305-*g*. For example, in some implementations, the magnetic component 825 may include a metal plate and ferrite tape disposed against a charger magnet.

In some aspects, as shown in FIG. 8, the magnetic component 825 and/or inductive component of the ring 104-*g* may be positioned underneath an outer circumferential surface of the ring 104-*j* (e.g., surface of ring 104-*j* facing away from a user's finger when worn) to improve wireless coupling with the magnetic component 820 and inductive components of the charging device 305-*g*. For example, as shown in FIG. 8, the magnetic component 825 and/or inductive component of the ring 104-*g* may be positioned underneath/behind one or more sensors 835 of the ring 104-*j*. This may be compared to the ring 104-*b* illustrated in FIG. 5, in which the magnetic component 525 and/or inductive component of the ring 104-*b* is positioned underneath an inner circumferential surface of the ring 104-*b* (e.g., surface of ring 104-*j* facing towards a user's finger when worn).

Due to the magnetic qualities of ferrite, the ferrite tape may serve as an inductive component and/or the magnetic component 825 of the wearable device 104-*j* to orient wearable device 104-*j* in a charging position within the sleeve 805 favorable for wireless charging. For example, a magnetic force may attract the magnetic component 825 and the magnetic components 820 to reduce a threshold distance between the inductive charging components 815 of charging device 305-*g* and one or more inductive charging components of wearable device 104-*j*, which may be located in a PCB 830. In some examples, the wearable device 104-*j* may include a PCB 830 that includes or otherwise connects one or more charging coils, a battery, one or more sensors 835, and a processor.

In some examples the magnetic components 820 of the base 905 may exert a tangential force on wearable device 104-*j*. The tangential force may arrange wearable device 104-*j* in a radial orientation for wireless charging (e.g., charging position). For example, the tangential force may rotate wearable device 104-*j* clockwise relative to an axis of the sleeve 805 or counterclockwise relative to an axis of the sleeve 805 in order to orient the wearable device 104-*j* in the charging position.

In some examples, one or more wires 840 or other conductive elements may connect sensors 535 (e.g., sensors used for collecting physiological data of a user) to PCB 830, which may include a logic board for wearable device 104-*b*. For example, the wires 840 may connect sensor 835-*a*, sensor 835-*b*, and sensor 835-*c* to PCB 830. The magnetic component 825 may be located at the front, or top, of wearable device 104-*j*. The magnetic component 825 may span a portion, or multiple portions, of the inner surface of wearable device 104-*j*. For example, the magnetic component 825 may be positioned to orient wearable device 104-*j* to a correct position for charging regardless of an orientation of wearable device 104-*j*. In some examples, charging device 305-*g* may have an external power source via a wired connection at 345.

Figure 9:
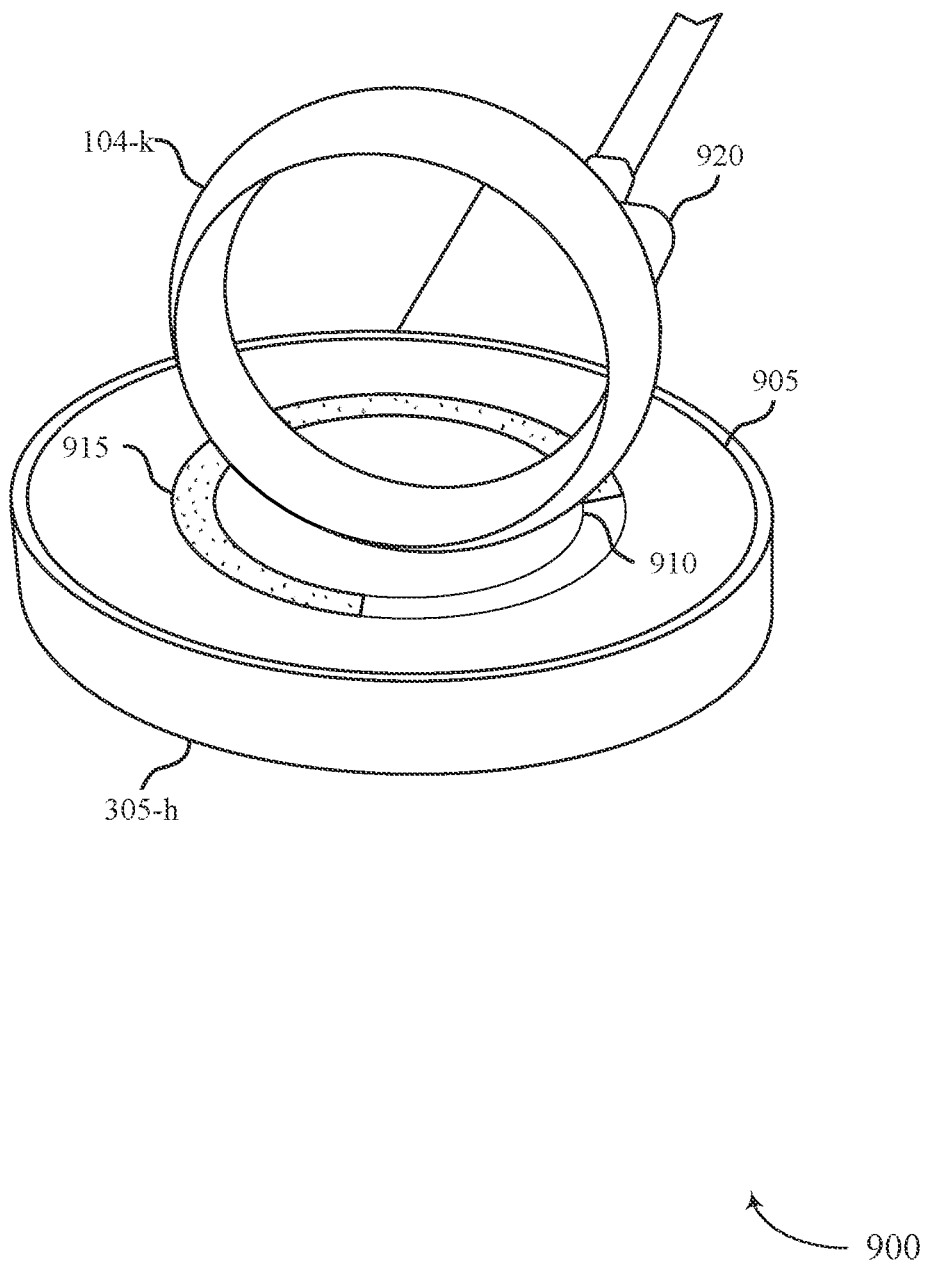

FIG. 9 illustrates an example of a charging diagram 900 that supports a universal charger in accordance with aspects of the present disclosure. The charging diagram 900 may implement, or be implemented by, aspects of the system 100, system 200, system 300, charging diagram 400 through charging diagram 800, or a combination thereof. For example, charging diagram 900 may illustrate examples of a wearable device 104-*k* and a charging device 305-*h*, which may be examples of a wearable device 104 and a charging device 305 as described with reference to FIG. 3. Specifically, the charging diagram 900 may illustrate use of a magnetic force to orient wearable device 104-k in a charging position. Although wearable device 104-k is illustrated as a ring in FIG. 9, wearable device 104-k may be any example of a wearable device 104 (e.g., a watch, necklace, bracelet, and the like).

In some examples, charging diagram 900 may include a charging device 305, such as charging device 305-h, which may charge a wearable device 104. Charging device 305-h may include a magnetic component to magnetically attract a magnetic component in wearable device 104-k. For example, a base 905 of charging device 305-h may include a magnet (e.g., a rare earth magnet, ferrite tape, a transmitter coil, or the like), such as at the middle of the base, and wearable device 104-k may include a similar magnet. The magnets or magnetic components may create a magnetic force to ensure a charging component of wearable device 104-k remains within a threshold distance of charging components of charging device 305-k located within the base 905.

In some cases, the magnetic components and charging components of charging device 305-h may be located at a center of a flat surface of the base 905. The base may include a depressed section where a wearable device 104 may rest. For example, base 905 may have a depressed section 910 (e.g., indent) where wearable device 104-k is aligned via a magnetic force. The size of the depressed section 910 may be based on a portion of wearable device 104-k. For example, the depressed section 910 may be a same size as a charging component, magnetic component, or both of wearable device 104-k. The magnets in wearable device 104-k and charging device 305-h may keep radial orientations of wearable device 104-k relative to an axis that is parallel to the flat surface.

In some examples, charging device 305-h may include one or more LEDs 915 to display a charging status. For example, a portion of LEDs 915 may blink while wearable device 104-k is actively charging, and may turn solid when wearable device 104-k has reached a maximum or threshold charge. Additionally or alternatively, a portion of the total number of LEDs 915 may light up to represent a battery percentage (e.g., if a battery is at 50%, 5 of 10 LEDs 915 may light up). In some cases, the LEDs 915 may indicate one or more alerts to the user (e.g., by changing colors, blinking, flashing). For example, the LEDs 915 may turn red if there is a charging malfunction, or the like. In some cases, the base 905 may be capable of charging multiple wearable devices 104. The LEDs 915 may indicate using different colors or flashing patterns which of the multiple rings may be charged.

In some examples, charging device 305-h may be a universal charger. That is, charging device 305-h may accommodate each manufactured size wearable device 104-k. The platform, or depressed section 910, may be manufactured to fit a wearable device 104 with a largest size. The base 905 may be any size or shape, such as round, rectangular (e.g., square), elliptical, or the like, to accommodate the wearable devices 104. In some examples, the charging device 305-h may be wired to a power source at 920. Additionally, or alternatively, the charging device 305-h may include a battery or other internal power source.

In some examples the magnetic component of the base 905 may exert a tangential force on wearable device 104-k. The tangential force may arrange wearable device 104-k in a radial orientation. For example, the tangential force may rotate wearable device 104-k to a vertical position perpendicular to the base, and clockwise relative to an axis of the base 905 and/or axis parallel to the base, counterclockwise relative to an axis of the base 905 and/or axis parallel to the base, or a combination thereof.

It should be noted that the methods described above describe possible implementations, and that the operations and the steps may be rearranged or otherwise modified and that other implementations are possible. Furthermore, aspects from two or more of the methods may be combined.

An apparatus for a universal charging device is described. The apparatus may include a base, a magnetic component, and an inductive charging component. The base may be configured to receive a ring-shaped wearable device in multiple radial orientations relative to the base. The magnetic component of the base may be configured to magnetically attract an additional magnetic component of the ring-shaped wearable device to orient the ring-shaped wearable device in a single radial orientation relative to the base from the multiple radial orientations when the ring-shaped wearable device is received by the base. The inductive charging component of the base may be configured to wirelessly charge the ring-shaped wearable device through inductive coupling with an additional inductive charging component of the ring-shaped wearable device when the ring-shaped wearable device is magnetically coupled with the base and radially oriented according to the single radial orientation, where the single radial orientation is configured to position the additional inductive charging component of the ring-shaped wearable device within a threshold distance from the inductive charging component of the base.

In some examples of the apparatuses described herein, the base includes a support component. The base may be further configured to couple the ring-shaped wearable device to the support component based on the ring-shaped wearable device at least partially surrounding the support component, where the multiple radial orientations may be defined relative to an axis of the support component. The support component may be adjustable in width, radius, circumference, or any combination thereof. The support component may be conical in shape.

In some examples of the apparatuses described herein, the magnetic component of the base may be further configured to exert a tangential force on the ring-shaped wearable device relative to an axis of the base based on interacting with the additional magnetic component of the ring-shaped wearable device, the tangential force arranging the ring-shaped wearable device in the single radial orientation. The tangential force may be configured to rotate the ring-shaped wearable device clockwise relative to the axis of the base, counter-clockwise relative to the axis of the base, or both In some examples of the apparatuses described herein, the base includes a sleeve component. The base may be further configured to couple the ring-shaped wearable device to the sleeve component based on the sleeve component at least partially surrounding the ring-shaped wearable device.

In some examples of the apparatuses described herein, the base includes a flat surface. The magnetic component may be positioned beneath the flat surface, and the base may be further configured to couple the ring-shaped wearable device to the flat surface based at least in part on the magnetic component of the base magnetically attracting the additional magnetic component of the ring-shaped wearable device when the ring-shaped wearable device is positioned on the flat surface, where the multiple radial orientations are relative to an axis that is parallel to the flat surface. The magnetic component of the base may magnetically attract the additional magnetic component of the ring-shaped wearable device along a direction perpendicular to the flat surface. The flat surface may include an indent configured to receive the ring-shaped wearable device, the indent including a size that is based on a portion of the ring-shaped wearable device.

In some examples, the inductive charging component of the base includes a transmitter coil, ferrite tape, or both.

In some examples, the magnetic component of the base includes multiple magnets arranged according to a pattern based at least in part on a polarity of each magnet of the multiple magnets.

In some examples, the threshold distance may be based on one or more parameters associated with the magnetic component, the additional magnetic component, or both.

Another apparatus for detecting contact with a wearable device is described. The apparatus may include charging system with a ring shaped wearable device and a base configured to receive the ring-shaped wearable device in multiple radial orientations relative to the base. The ring-shaped wearable device includes a first magnetic component and a first inductive component. The base includes a second magnetic component configured to magnetically attract the first magnetic component of the ring-shaped wearable device to orient the ring-shaped wearable device in a single radial orientation relative to the base from the plurality of radial orientations when the ring-shaped wearable device is received by the base and a second inductive component configured to wirelessly charge the ring-shaped wearable device through inductive coupling with the first inductive component of the ring-shaped wearable device when the ring-shaped wearable device is magnetically coupled with the base and radially oriented according to the single radial orientation, where the single radial orientation is configured to position the first inductive component of the ring-shaped wearable device within a threshold distance from the second inductive component of the base.

In some examples of the apparatuses described herein, the base includes a support component. The base may be further configured to couple the ring-shaped wearable device to the support component based on the ring-shaped wearable device at least partially surrounding the support component, where the multiple radial orientations may be defined relative to an axis of the support component.

In some examples, the second magnetic component may be further configured to exert a tangential force relative to an axis of the base based on interacting with the first magnetic component, the tangential force arranging the ring-shaped wearable device in at least one radial orientation of the multiple radial orientations. The tangential force may be configured to rotate the ring-shaped wearable device clockwise relative to the axis of the base, counter-clockwise relative to the axis of the base, or both.

In some examples of the apparatuses described herein, the base includes a sleeve component. The base may be further configured to couple the ring-shaped wearable device to the sleeve component based on the sleeve component at least partially surrounding the ring-shaped wearable device.

In some examples of the apparatuses described herein, the base includes a flat surface. The second magnetic component may be positioned beneath the flat surface, and the base may be further configured to couple the ring-shaped wearable device to the flat surface based on the second magnetic component of the base magnetically attracting the first magnetic component of the ring-shaped wearable device when the ring-shaped wearable device is positioned on the flat surface, where the plurality of radial orientations are relative to an axis that is parallel to the flat surface. The second magnetic component of the base may magnetically attract the first magnetic component of the ring-shaped wearable device along a direction perpendicular to the flat surface. The flat surface may include an indent configured to receive the ring-shaped wearable device, the indent comprising a size that is based on a portion of the ring-shaped wearable device.

In some examples, the second inductive component of the base includes a transmitter coil, ferrite tape, or both.

In some examples, the first magnetic component of the ring-shaped wearable device, the first inductive component of the ring-shaped wearable device, or both, include ferrite tape, where the second magnetic component of the base may be configured to magnetically attract the ferrite tape to orient the ring-shaped wearable device in the single radial orientation.

In some examples, the first magnetic component of the ring-shaped wearable device, the second magnetic component of the base, or both, include multiple magnets arranged according to a pattern based at least in part on a polarity of each magnet of the multiple magnets.

In some examples, the second inductive component of the base may be positioned beneath an outer surface of the base, and where the first inductive component of the ring-shaped wearable device is positioned beneath an inner surface associated with an inner circumference of the ring-shaped wearable device.

In some examples, the first inductive component of the ring-shaped wearable device includes a receiver coil, and where the second inductive component of the base includes a transmitter coil configured to inductively interact with the receiver coil of the ring-shaped wearable device to wirelessly charge the ring-shaped wearable device.

In some examples, the first magnetic component and the first inductive component of the ring-shaped wearable device are the same.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A charging device, comprising:
   a base comprising a support component and configured to receive a ring-shaped wearable device in a plurality of radial orientations relative to the base based on the ring-shaped wearable device at least partially surrounding the support component;
   a magnetic component of the base configured to magnetically attract an additional magnetic component of the ring-shaped wearable device to automatically orient the ring-shaped wearable device in a single radial orientation relative to the base from the plurality of radial orientations when the ring-shaped wearable device is received by the base; and
   an inductive charging component of the base configured to wirelessly charge the ring-shaped wearable device through inductive coupling with an additional inductive charging component of the ring-shaped wearable device when the ring-shaped wearable device is magnetically coupled with the base and radially oriented according to the single radial orientation, wherein the single radial orientation is configured to position the additional inductive charging component of the ring-shaped wearable device within a threshold distance from the inductive charging component of the base.

2. The charging device of claim 1, wherein the base is further configured to:
   couple the ring-shaped wearable device to the support component based on the ring-shaped wearable device at least partially surrounding the support component, wherein the plurality of radial orientations are defined relative to an axis of the support component.

3. The charging device of claim 2, wherein the support component is adjustable in width, radius, circumference, or any combination thereof.

4. The charging device of claim 2, wherein the support component is conical in shape.

5. The charging device of claim 1, wherein the magnetic component of the base is further configured to:
   exert a tangential force on the ring-shaped wearable device relative to an axis of the base based at least in part on interacting with the additional magnetic component of the ring-shaped wearable device, the tangential force arranging the ring-shaped wearable device in the single radial orientation.

6. The charging device of claim 5, wherein the tangential force is configured to rotate the ring-shaped wearable device clockwise relative to the axis of the base, counter-clockwise relative to the axis of the base, or both.

7. The charging device of claim 1, wherein the base comprises a flat surface, and wherein the magnetic component is positioned beneath the flat surface, the base further configured to:
   couple the ring-shaped wearable device to the flat surface based at least in part on the magnetic component of the base magnetically attracting the additional magnetic component of the ring-shaped wearable device when the ring-shaped wearable device is positioned on the flat surface, wherein the plurality of radial orientations are relative to an axis that is parallel to the flat surface.

8. The charging device of claim 7, wherein the magnetic component of the base magnetically attracts the additional magnetic component of the ring-shaped wearable device along a direction perpendicular to the flat surface.

9. The charging device of claim 7, wherein the flat surface comprises an indent configured to receive the ring-shaped wearable device, the indent comprising a size that is based at least in part on a portion of the ring-shaped wearable device.

10. The charging device of claim 1, wherein the inductive charging component of the base comprises a transmitter coil, ferrite tape, or both.

11. The charging device of claim 1, wherein the magnetic component of the base comprises a plurality of magnets arranged according to a pattern based at least in part on a polarity of each magnet of the plurality of magnets.

12. The charging device of claim 1, wherein the threshold distance is based at least in part on one or more parameters associated with the magnetic component, the additional magnetic component, or both.

13. A charging device, comprising:
a base comprising a sleeve component and configured to receive a ring-shaped wearable device in a plurality of radial orientations relative to the base and couple the ring-shaped wearable device to the sleeve component based on the sleeve component at least partially surrounding the ring-shaped wearable device;
a magnetic component of the base configured to magnetically attract an additional magnetic component of the ring-shaped wearable device to orient the ring-shaped wearable device in a single radial orientation relative to the base from the plurality of radial orientations when the ring-shaped wearable device is received by the base; and
an inductive charging component of the base configured to wirelessly charge the ring-shaped wearable device through inductive coupling with an additional inductive charging component of the ring-shaped wearable device when the ring-shaped wearable device is magnetically coupled with the base and radially oriented according to the single radial orientation, wherein the single radial orientation is configured to position the additional inductive charging component of the ring-shaped wearable device within a threshold distance from the inductive charging component of the base.

14. A charging system, comprising:
a ring-shaped wearable device, comprising:
a first magnetic component; and
a first inductive component; and
a base configured to receive the ring-shaped wearable device in a plurality of radial orientations relative to the base, the base comprising:
a support component, wherein the base is configured to receive the ring-shaped wearable device in the plurality of radial orientations based on the ring-shaped wearable device at least partially surrounding the support component;
a second magnetic component configured to magnetically attract the first magnetic component of the ring-shaped wearable device to automatically orient the ring-shaped wearable device in a single radial orientation relative to the base from the plurality of radial orientations when the ring-shaped wearable device is received by the base; and
a second inductive component configured to wirelessly charge the ring-shaped wearable device through inductive coupling with the first inductive component of the ring-shaped wearable device when the ring-shaped wearable device is magnetically coupled with the base and radially oriented according to the single radial orientation, wherein the single radial orientation is configured to position the first inductive component of the ring-shaped wearable device within a threshold distance from the second inductive component of the base.

15. The charging system of claim 14, wherein the is further configured to:
couple the ring-shaped wearable device to the support component based on the ring-shaped wearable device at least partially surrounding the support component, wherein the plurality of radial orientations are defined relative to an axis of the support component.

16. The charging system of claim 14, wherein the second magnetic component is further configured to:
exert a tangential force relative to an axis of the base based at least in part on interacting with the first magnetic component, the tangential force arranging the ring-shaped wearable device in at least one radial orientation of the plurality of radial orientations.

17. The charging system of claim 16, wherein the tangential force is configured to rotate the ring-shaped wearable device clockwise relative to the axis of the base, counterclockwise relative to the axis of the base, or both.

18. The charging system of claim 14, wherein the base comprises a flat surface, and wherein the second magnetic component is positioned beneath the flat surface, the base further configured to:
couple the ring-shaped wearable device to the flat surface based at least in part on the second magnetic component of the base magnetically attracting the first magnetic component of the ring-shaped wearable device when the ring-shaped wearable device is positioned on the flat surface, wherein the plurality of radial orientations are relative to an axis that is parallel to the flat surface.

19. The charging system of claim 18, wherein the second magnetic component of the base magnetically attracts the first magnetic component of the ring-shaped wearable device along a direction perpendicular to the flat surface.

20. The charging system of claim 18, wherein the flat surface comprises an indent configured to receive the ring-shaped wearable device, the indent comprising a size that is based at least in part on a portion of the ring-shaped wearable device.

21. The charging system of claim 14, wherein the second inductive component of the base comprises a transmitter coil, ferrite tape, or both.

22. The charging system of claim 14, wherein the first magnetic component of the ring-shaped wearable device, the first inductive component of the ring-shaped wearable device, or both, comprises ferrite tape, wherein the second magnetic component of the base is configured to magnetically attract the ferrite tape to orient the ring-shaped wearable device in the single radial orientation.

23. The charging system of claim 14, wherein the first magnetic component of the ring-shaped wearable device, the second magnetic component of the base, or both, comprise a plurality of magnets arranged according to a pattern based at least in part on a polarity of each magnet of the plurality of magnets.

24. The charging system of claim 14, wherein the second inductive component of the base is positioned beneath an outer surface of the base, and wherein the first inductive component of the ring-shaped wearable device is positioned beneath an inner surface associated with an inner circumference of the ring-shaped wearable device.

25. The charging system of claim 14, wherein the first inductive component of the ring-shaped wearable device comprises a receiver coil, and wherein the second inductive component of the base comprises a transmitter coil configured to inductively interact with the receiver coil of the ring-shaped wearable device to wirelessly charge the ring-shaped wearable device.

26. The charging system of claim 14, wherein the first magnetic component and the first inductive component of the ring-shaped wearable device are the same.

27. A charging system, comprising:
- a ring-shaped wearable device, comprising:
  - a first magnetic component; and
  - a first inductive component; and
- a base configured to receive the ring-shaped wearable device in a plurality of radial orientations relative to the base, the base comprising:
  - a sleeve component, wherein the base is configured to couple the ring-shaped wearable device to the sleeve component based on the sleeve component at least partially surrounding the ring-shaped wearable device;
  - a second magnetic component configured to magnetically attract the first magnetic component of the ring-shaped wearable device to orient the ring-shaped wearable device in a single radial orientation relative to the base from the plurality of radial orientations when the ring-shaped wearable device is received by the base; and
  - a second inductive component configured to wirelessly charge the ring-shaped wearable device through inductive coupling with the first inductive component of the ring-shaped wearable device when the ring-shaped wearable device is magnetically coupled with the base and radially oriented according to the single radial orientation, wherein the single radial orientation is configured to position the first inductive component of the ring-shaped wearable device within a threshold distance from the second inductive component of the base.

* * * * *